(12) United States Patent
Ahmad et al.

(10) Patent No.: US 8,771,322 B2
(45) Date of Patent: Jul. 8, 2014

(54) CRANIAL FLAP FIXATION SYSTEM AND METHOD

(75) Inventors: Shaher A. Ahmad, Plano, TX (US); Lisa Regina Thornhill, Dallas, TX (US); Jon M. Staples, Coppell, TX (US)

(73) Assignee: OsteoMed LLC, Addison, TX (US)

( * ) Notice: Subject to any disclaimer, the term of this patent is extended or adjusted under 35 U.S.C. 154(b) by 1175 days.

(21) Appl. No.: 12/334,586

(22) Filed: Dec. 15, 2008

(65) Prior Publication Data

US 2009/0093812 A1    Apr. 9, 2009

Related U.S. Application Data

(63) Continuation of application No. 11/006,873, filed on Dec. 8, 2004, now Pat. No. 7,476,241, which is a continuation-in-part of application No. 10/407,890, filed on Apr. 4, 2003, now Pat. No. 7,387,633.

(51) Int. Cl.
*A61B 17/80* (2006.01)

(52) U.S. Cl.
USPC .............................. 606/280; 606/301; 606/324

(58) Field of Classification Search
USPC ................ 606/60, 280, 70, 71, 281–299, 104
See application file for complete search history.

(56) References Cited

U.S. PATENT DOCUMENTS

| | | | |
|---|---|---|---|
| 5,391,171 A | 2/1995 | Schmieding | 606/104 |
| 5,800,436 A | 9/1998 | Lerch | 606/72 |
| 6,022,351 A | 2/2000 | Bremer et al. | 606/72 |
| 6,068,631 A | 5/2000 | Lerch | 606/72 |
| 6,258,091 B1 | 7/2001 | Sevrain et al. | 606/72 |
| 6,379,363 B1 | 4/2002 | Herrington et al. | 606/79 |
| 6,423,073 B2 | 7/2002 | Bowman | 606/104 |
| 6,685,707 B2 | 2/2004 | Roman et al. | 606/72 |
| 6,755,834 B2 | 6/2004 | Amis | 606/72 |
| 2002/0016593 A1 | 2/2002 | Hearn | 606/72 |
| 2002/0062128 A1 | 5/2002 | Amis | 606/72 |
| 2003/0229349 A1 | 12/2003 | Wellisz et al. | 606/72 |

FOREIGN PATENT DOCUMENTS

DE    20101793 U1    6/2001

OTHER PUBLICATIONS

RapidFlap™ presented by W.Lorez Surgical http://www.lorenzsurgical.com/NS_rapidflap.html, Apr. 26, 2002.
"CranioFix®-Impant System for Refixation of Cranial Bone Flaps After Craniotomy", Copyright © Aesculap AG & Co, KG 1996-2001, http://www.aesculap.com/e/produkte/chir/neuro/verschluss/craniofix/chp_cran.htm, Apr. 26, 2002.
Notification of Transmittal of the International Search Report and Written Opinion, International Application No. PCT/US2004/009795, filed Mar. 31, 2004 (7 pages), Aug. 10, 2004.

*Primary Examiner* — Mary Hoffman
(74) *Attorney, Agent, or Firm* — Fulbright & Jaworski LLP

(57) ABSTRACT

A cranial flap fixation system and method are provided. In one embodiment, the system includes a rod having first and second ends, and an intermediate portion. The rod has a threaded portion between the first end and the intermediate portion. The system also includes an inferior disk coupled with the rod, proximate the first end of the rod, and a superior disk with an orifice through a central region of the superior disk. The orifice is sized to allow the superior disk to engage the threaded portion and movably couple the superior disk to the rod. The system further includes an installation tool having a central cavity. The installation tool is configured to engage the superior disk and the threaded portion, such that rotation of the installation tool in a first direction directs the superior disk toward the inferior disk.

15 Claims, 3 Drawing Sheets

CRANIAL FLAP FIXATION SYSTEM AND METHOD

RELATED APPLICATIONS

This application is a continuation of U.S. application Ser. No. 11/006,873, filed Dec. 8, 2004 and entitled "Cranial Flap Fixation System and Method," which is a continuation-in-part of U.S. application Ser. No. 10/407,890, filed Apr. 4, 2003, now U.S. Pat. No. 7,387,633, issued Jun. 17, 2008 and entitled "Cranial Flap Fixation System and Method."

TECHNICAL FIELD OF THE INVENTION

The present invention relates in general to the field of surgical fixation devices, and, in particular, to a cranial flap fixation system and method.

BACKGROUND OF THE INVENTION

To gain access to the brain for neurosurgical procedures, holes are often cut in the skull. These holes are created by making one or more bur holes in the cranial bone and then cutting the bone to connect the bur holes. The segment of the cranial bone removed in this fashion is referred to as a cranial flap. Once the surgical procedure is complete, however, the cranial flap must be repositioned in the cavity created by its removal. This is done by placing the cranial flap in its original position and fastening the flap to the surrounding cranial bone.

Currently a number of methods for cranial flap fixation exist. One such method utilizes clamping designs to close the cranial flap. Generally, these designs consist of two circular disks that are attached via a stem or connecting rod. The cranial flap is fixated by squeezing the flap, along with the surrounding cranial bone, between the two disks. However, many current clamping designs are limited in that they use ratcheting mechanisms which have a finite displacement and have the potential to apply excessive force to the cranial flap and surrounding cranial bone. Furthermore, most existing clamping designs do not address the need to return to the surgical site without undue effort. Instead, they require instruments to pry the top disks from the stem. In addition, many current clamping designs require instrumentation that requires additional maintenance, cleaning, and sterilization, adding to the time hospitals must dedicate to such devices.

SUMMARY OF THE INVENTION

In accordance with the present invention, a cranial flap fixation system and method are provided. In one embodiment, the system includes a connecting rod having a first and second end, and an intermediate portion. The connecting rod has a threaded portion between the first end and the intermediate portion. The system also includes an inferior disk coupled with the connecting rod, proximate the first end of the connecting rod, and a superior disk with an orifice through a central region of the superior disk. The orifice is sized to allow the superior disk to engage the threaded portion and movably couple the superior disk to the connecting rod. The system further includes an installation tool having a central cavity. The installation tool is configured to engage the superior disk and the threaded portion, such that rotation of the installation tool in a first direction forces the superior disk toward the inferior disk.

In an alternative embodiment, the system includes a tool body having a first and second end, and an intermediate portion. The tool body has a reduced diameter portion between the first end and the intermediate portion. An at least partially threaded bore passes through the center of the tool body from the first end to the second end. The tool body also includes at least two opposing angled faces disposed on the first end of the tool body and adjacent the reduced diameter portion. The angled faces are configured to accommodate tilting of the tool body relative to a horizontal plane perpendicular to the axis of the tool body. The tool body further includes at least two opposing tapered surfaces on the first end of the tool body and alternatingly arranged with the angled faces. The tapered surfaces are operable to reduce the profile of the first end.

A method of fixing a cranial flap, in accordance with the present invention, may include coupling an inferior disk proximate to a first end of a connecting rod. The connecting rod may have a second end and an intermediate portion between the first end and the second end. The connecting rod may also have a threaded portion between the first end and the intermediate portion. The method may then couple a superior disk to the connecting rod. The superior disk may have an orifice through a central region of the superior disk. The orifice may be sized to allow the superior disk to engage the threaded portion and movably couple the superior disk to the connecting rod. The method may also include coupling an installation tool to the connecting rod. The installation tool may have a central cavity extending therethrough. The installation tool may also be configured to engage the superior disk and the threaded portion, such that rotation of the installation tool in a first direction forces the superior disk toward the inferior disk. The method may also include positioning the inferior disk on a first side of a cranial flap and adjacent cranial bone, and positioning the superior disk on a second side of the cranial flap and adjacent cranial bone, and rotating the installation tool relative to the connecting rod such that the inferior and superior disks are brought in contact with the first and second sides, respectively, and the inferior and superior disks apply pressure to the cranial flap and adjacent cranial bone.

Technical advantages of particular embodiments of the present invention include a cranial flap fixation system and method that provide enhanced variability in the amount of pressure applied to a cranial flap and adjacent cranial bone depending on how tightly the superior and inferior disks are brought together. Such variability is enhanced by providing a threaded superior disk with practically infinite adjustability as compared to a "ratchet" type system. This variability allows surgeons to select the appropriate amount of pressure to apply along a cranial flap joint without being limited by the design of the fixation device.

Another technical advantage of particular embodiments of the present invention is a disposable installation tool that may be used to install the fixation device, as well as remove the excess portion of the connecting rod that is left after installation. This dual functionality of the installation tool allows for quicker installations of the device and eliminates several time consuming steps found in typical fixation device installations.

Yet another technical advantage of particular embodiments of the present invention is a cranial flap fixation device that greatly reduces the risk of fixation device loosening over time. In accordance with a particular embodiment, this is accomplished using a downward-facing tab on the superior disk of the fixation device configured to reside in the gap between the cranial flap and the adjacent cranial bone and resist any rotation of the superior disk.

Still another technical advantage of particular embodiments of the present invention is a cranial flap fixation device that includes a plurality of flange-forming slots situated radially around the inferior disk. These slots allow the inferior disk to adapt to the curvature of the cranium and form a close fit with the concave underside of the skull.

Other technical advantages will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the present invention and its advantages, reference is now made to the following descriptions, taken in conjunction with the accompanying drawings, in which.

DETAILED DESCRIPTION OF THE INVENTION

Figure 1:
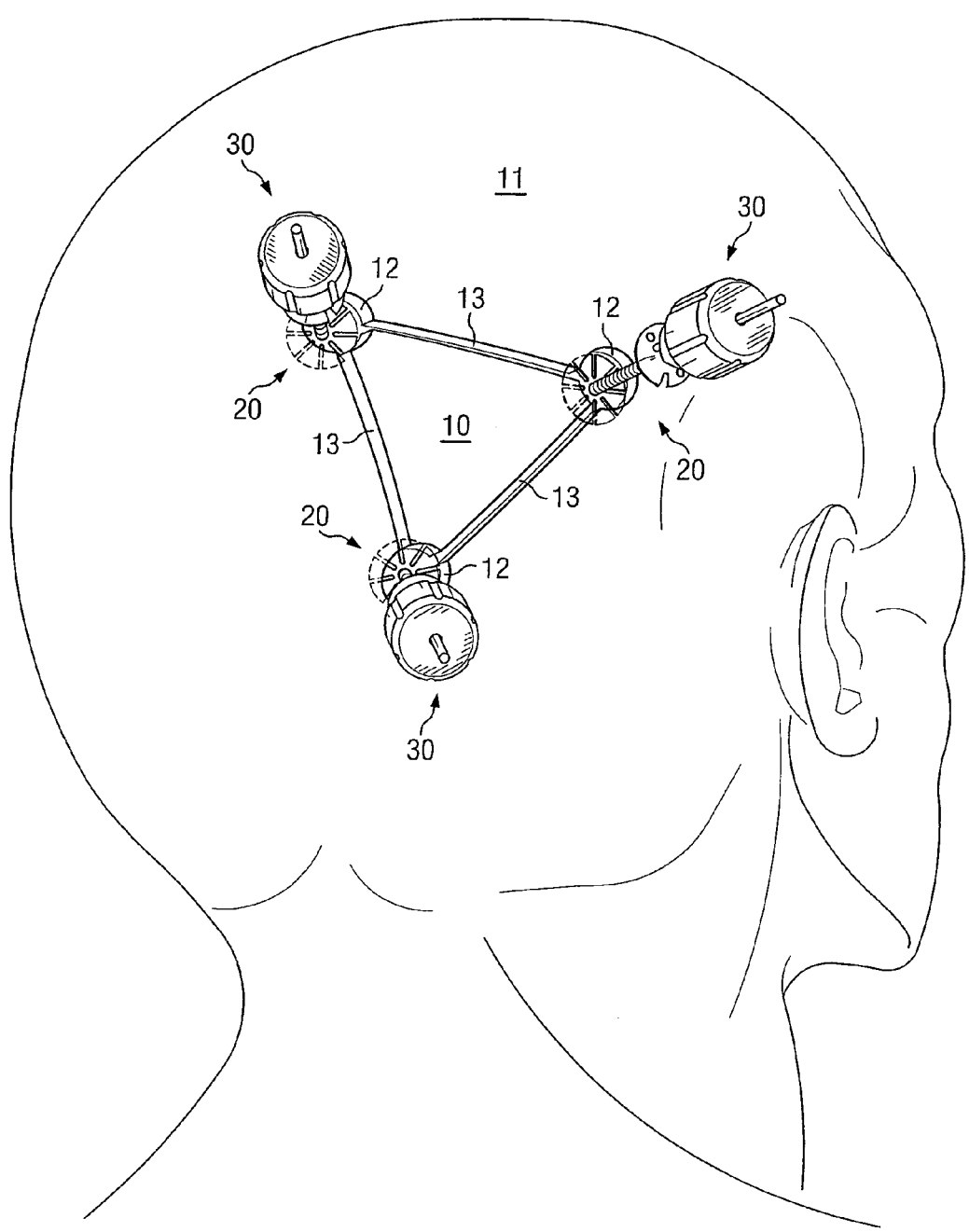
FIG. 1 illustrates a plurality of cranial flap fixation devices and installation tools, in accordance with a particular embodiment of the present invention, disposed within a cranial flap joint.

FIG. 1 illustrates a plurality of cranial flap fixation devices in accordance with a particular embodiment of the present invention. Cranial flap fixation device 20 is a fastening system used to fixate a cranial flap to the surrounding cranial bone following a craniotomy. In particular, fixation device 20 includes two circular disks that are attached via a threaded connecting rod. A cranial flap is fixated by being squeezed, along with the surrounding cranial bone, between the two disks. Due to the threaded connection between the connecting rod and the disks, fixation device 20 offers practically infinite adjustability and, therefore, enhanced variability in the amount of pressure applied to the cranium by the two circular disks. Fixation device 20 may also be configured for use with a disposable installation tool 30, which may be used to tighten the device as well as remove the excess portion of the connecting rod left after installation.

As shown in FIG. 1, a plurality of cranial flap fixation devices 20 are used to fixate cranial flap 10 to the surrounding cranial bone 11. Cranial flap 10 is originally created by creating a plurality of bur holes 12 in the cranium, and connecting the holes by a plurality of cuts 13. With bur holes 12 connected, the resulting cranial flap 10 may be removed so that a neurosurgical procedure may be performed. Following the procedure, however, it is often desirable to reposition cranial flap 10 in the cavity formed by its removal and fixate it to the surrounding cranial bone 11.

To fixate cranial flap 10 to surrounding cranial bone 11, a plurality of fixation devices 20 are used. Prior to replacing cranial flap 10, one fixation device 20 is placed in each bur hole 12 at the corners of flap 10. As shown in FIG. 1, each fixation device 20 is in the loosened position. With the fixation devices 20 in this loosened position, the inferior disk 21 (FIG. 2) of each fixation device 20 is positioned within the interior of cranial bone 11, while the superior disk 22 (FIG. 2) of each device 20 is positioned above the exterior of cranial bone 11.

With the fixation devices in place, cranial flap 10 is then repositioned in the cavity formed by its removal. Once cranial flap 10 is repositioned in its cavity, the plurality of fixation devices 20 are tightened, bringing the disks 21 and 22 in intimate contact with the cranium. Once fixation device 20 is tightened, the excess portions of connecting rods 23 extending above superior disk 22 (FIG. 2) are removed. So installed, fixation devices 20 provide a rigid fixation of cranial flap 10 to surrounding cranial bone 11.

Figure 2:
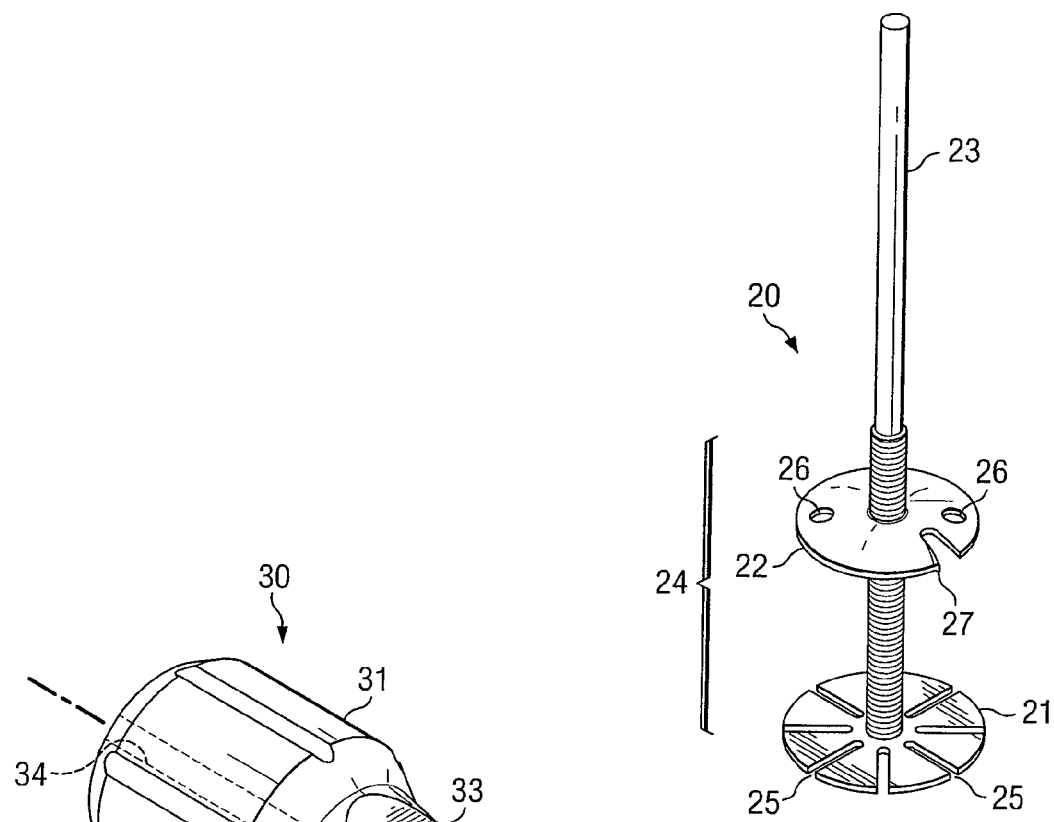
FIG. 2 illustrates a cranial flap fixation device in accordance with a particular embodiment of the present invention.

FIG. 2 illustrates a close up view of fixation device 20 in accordance with a particular embodiment of the present invention. As shown in FIG. 2, fixation device 20 includes connecting rod 23. Connecting rod 23 includes threaded region 24, which extends from one end of rod 23 at least partially up the rod towards the other end. Designed to be implanted in the human body, connecting rod 23 may be constructed of a number of implantable materials. In the illustrated embodiment, rod 23 comprises a non-resorbable material, although many other materials are available for use. These include titanium alloys, nickel-titanium alloys, such as Nitinol (NiTi) stainless steel, plastics, metals and other alloys or combinations thereof. These allow connecting rod 23 to have ample strength to withstand the pressure applied once installed, yet be intentionally fractured to remove the excess portion of the rod left after fixation device 20 is tightened. It should be recognized, though, that connecting rod 23 may be constructed using one or more of a variety of materials.

Connecting rod 23 is formed of a material operable to fracture in response to bending forces. By bending rod 23 and applying tensile force thereto, a clean break may be formed adjacent the top of the superior disk, such that little or none of the excess rod extends above an area adjacent the top of the superior disk.

Fixation device 20 also includes inferior disk 21. Inferior disk 21 is coupled to the threaded end of connecting rod 23, and is typically constructed of titanium alloy or another suitable implantable material. The coupling of inferior disk 21 and connecting rod 23 is provided by a central portion of the inferior disk that forms central orifice 28. The central portion is configured to be threadably coupled with the threaded end of connecting rod 23 such that inferior disk 21 is generally flush with the end of connecting rod 23. This threaded connection may further be welded, providing the additional benefit of a stronger coupling between inferior disk 21 and connecting rod 23 and preventing any rotation of inferior disk 21 relative to connecting rod 23.

Inferior disk 21 also includes a plurality of flange-forming slots 25 radially situated around the circumference of inferior disk 21. These slots 25 extend from a region near the central orifice 28 outwards through the circumference of inferior disk 21. This results in the inferior disk 21 having in a generally flower-like shape, as illustrated in FIG. 2. Inferior disk 21 is also formed from a thin, malleable material that allows inferior disk 21 to change shape and conform to a surface(s), without fracturing. When positioned within the interior of the cranial bone and exposed to adequate pressure, the flanges formed by slots 25 adapt inferior disk 21 to match the curvature of the interior of the cranium and form a close fit to the concave underside of the skull.

Fixation device 20 also includes superior disk 22. Constructed of titanium alloy or another suitable implantable material, superior disk 22 is configured to contact the exterior of the cranium when fixation device 20 is used to fixate cranial flap 10 to the surrounding cranial bone 11. Superior disk 22 may also be formed of a generally malleable material such that superior disk 22 may change shape and conform to the surface of the skull, in response to pressure being applied thereto.

Superior disk 22 includes a central portion that defines a central orifice 29. The central portion is configured to be threadably coupled with threaded region 24 of connecting rod 23. This allows superior disk 22 to be rotated relative to the connecting rod 23 and brought closer to inferior disk 21, tightening the fixation device.

Superior disk 22, which has a smooth circumference, also includes a concave downward-facing radius (i.e., superior disk 22 is concave with respect to inferior disk 21). This downward-facing concavity reduces the overall assembly height of fixation device 20 and aids in reducing the potential for soft tissue irritation when soft tissue comes in contact with fixation device 20.

Superior disk 22 also includes an anti-rotation device in the form of a downward-facing tab 27, which is configured to be aligned with joint 13 between cranial flap 10 and surrounding cranial bone 11 (see FIG. 1). This provides the additional benefit of inhibiting the rotation of fixation device 20 after installation. Rotation counter to the direction of rotation for installation would loosen the connecting rod 23/superior disk 22 assembly. Tab 27 prevents this reverse rotation because tab 27 faces a direction counter to the direction of rotation and sits in joint 13 so as to prevent reverse rotation. This allows for greater stability for the assembly once installed. In FIG. 2, tab 27 is shown as being formed by a slot in superior disk 22, the material on one side of the slot pushed downward. However, it should be recognized that tab 27 may be formed by other methods as well.

Various configurations and techniques are available to prevent rotation of superior disk 22 with respect to connecting rod 23, in lieu of or in addition to tab 27. For example, a non rotation device such as a detent may be coupled with superior disk 22. Tab 27 and/or the non rotation device may be used to prevent excessive tightening of superior disk 22, inadvertent loosening of superior disk 22 and/or an indicator that superior disk 22 is installed in the proper position relative to adjacent bone.

To assist in the tightening of fixation device 20, superior disk 22 also includes a plurality of guide holes 26. As shown in FIG. 2, two guide holes 26 are radially disposed on superior disk 22, approximately 180 degrees from each other, and approximately 90 degrees from the aforementioned tab 27. As will be discussed in greater detail below, these guide holes 26 may be designed to mate with pins from an installation tool, allowing superior disk 22 to be rotated relative to connecting rod 23. As superior disk 22 is rotated relative to connecting rod 23, superior disk 22 may be brought closer to inferior disk 21, until both disks 21 and 22 are in intimate contact with the cranium.

Figure 3:
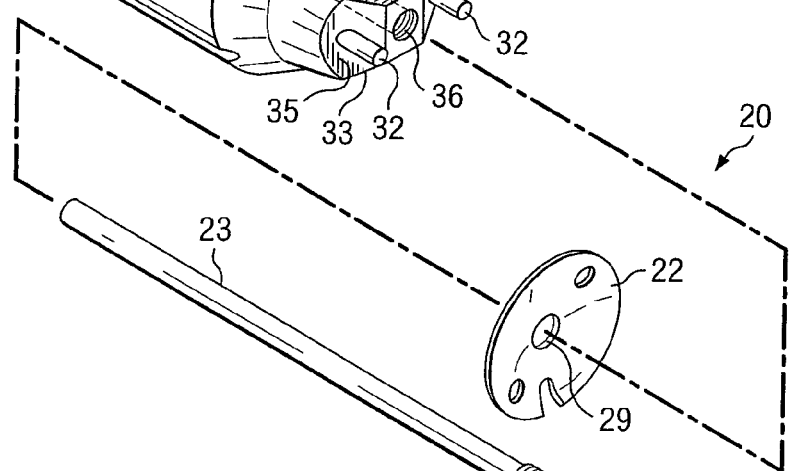
FIG. 3 illustrates the cranial flap fixation device shown in FIG. 2, along with an installation tool in accordance with a particular embodiment of the present invention.
Figure 3:
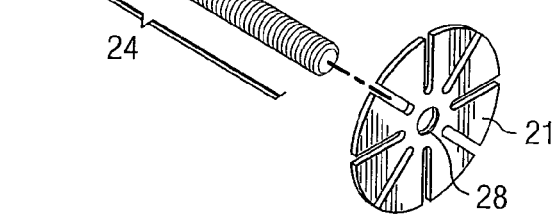

FIG. 3 illustrates disposable installation tool 30 in accordance with a particular embodiment of the present invention. As mentioned above, installation tool 30 may be used to tighten fixation device 20. Installation tool 30 offers the additional functionality of being able to remove the excess portion of connecting rod 23 left after device 20 is tightened and brought in intimate contact with the cranium. Furthermore, in order to reduce the amount of time spent maintaining, cleaning, and sterilizing the instrumentation used to install fixation device 20, installation tool 30 may also be configured to be pre-attached to fixation device 20, and may be intended to be disposed of after fixation device 20 is installed.

As shown in FIG. 3, installation tool 30 includes tool grip 31, which provides a handle for a surgeon to grip while tightening fixation device 20. As such, tool grip 30 may include a plurality of grooves longitudinally disposed on the exterior of the grip 30, providing a surface for a surgeon to grip. In alternative embodiments, other gripping features may be used in lieu of or in addition to the longitudinal grooves. For example, knurled surfaces and/or other indentations may be provided. Moreover, installation tool 30 may be configured to cooperate with a power instrument to rotate the installation tool with respect to rod 23. Such a power instrument may include a torque limiting device. Furthermore, grip 31 may be constructed of a number of surgical grade materials, such as metal, plastic, alloys, or a combination thereof.

Running down the longitudinal axis of tool grip 31 is central cavity 34, which is operable to receive the portion of connecting rod 23 extending above superior disk 22. In this way, the excess portion of connecting rod 23 provides a convenient site to install tool 30 on fixation device 20 prior to installation.

Central cavity 34 includes a threaded region 36 located near the opening of the cavity adjacent to superior disk 22. This threaded region 36 allows installation tool 30 to be threadably coupled with connecting rod 23, helping to ensure installation tool 30 will not decouple from connecting rod 23 prior to installation of fixation device 20, and allowing installation tool 30 to retain the excess portion of connecting rod 23 that is removed when installation tool 30 is used to trim connecting rod 23 following installation.

Installation tool 30 also includes a plurality of pins 32 which engage the plurality of guide holes 26 located on superior disk 22. Because of this engagement, when installation tool 30 is rotated around the longitudinal axis of connecting rod 23, superior disk 22 is also rotated relative to connecting rod 23. This rotation of installation tool 30 and superior disk 22 is continued until superior disk 22 and inferior disk 21 are in intimate contact with the cranium and tab 27 of superior disk 22 is lodged in the gap between cranial flap 10 and the surrounding cranial bone 11.

Due to the threaded connection between connecting rod 23 and superior disk 22, fixation device 20 provides practically infinite adjustability. By rotating superior disk 22 along the threads, practically any distance may be established between superior disk 22 and inferior disk 21. This provides greater adjustability than "ratchet-type" systems, and offers enhanced variability in the amount of pressure that may be applied by superior disk 22 and inferior disk 21 on cranial flap 10 and surrounding cranial bone 11. The threaded connection also allows fixation device 20 to be easily removed if needed.

As mentioned above, installation tool 30 may also be used to remove the excess portion of connecting rod 23 after fixation device 20 has been brought in intimate contact with the cranium. To help accomplish this, installation tool 30 also includes two opposing angled faces 33 disposed adjacent the superior disk. In the illustrated embodiment, angled faces 33 form an approximately 90-degree angle with each other and contact superior disk 22. These angled faces 33 are used as a guide for installation tool 30 when installation tool 30 is used to remove the excess portion of connecting rod 23. Once fixation device 20 is securely fastened to the cranium, installation tool 30 is tilted first in one direction and then in the opposite direction, using angled faces 33 as a guide. Threaded region 36, pins 32, and a set of tapered surfaces 35, located on installation tool 30 perpendicular to angled faces 33, all serve to isolate and focus the bending forces created by this tilting against connecting rod 23. This back and forth bending is continued until it results in the intentional fracturing of connecting rod 23.

Tapered surfaces 35 are also configured to allow installation tool 30 to be positioned more closely to superior disk 22.

This accommodates fracture of rod 23 at a position adjacent to the superior disk 22, and decreases an amount of the rod that extends beyond superior disk 22.

Because of the forces created by the back and forth bending of tool 30 upon rod 23, it is important to avoid placing excessive pressure on cranial flap 10 or the joint between it and the surrounding cranial bone 11. Such excessive pressure could bend the flap or put undesirable pressure on the brain. Therefore, guide holes 26 and tab 27 of superior disk 22 are configured to minimize the force exerted on the cranial flap 10 itself. As part of this configuration guide holes 26 and oriented approximately 90 degrees from tab 27. Due to this orientation, when tab 27 is aligned with gap 13 between cranial flap 10 and surrounding cranial bone 11, guide holes 26 straddle gap 13. Because of this, when pins 32 of the installation tool engage guide holes 26, installation tool 30 is prevented from leveraging against cranial flap 10. Instead, the back and forth bending results in leveraging along gap 13, rather than towards one side or the other of gap 13.

Because of the mechanics employed in the fracture of connecting rod 23, the fracture of rod 23 results in a relatively flat surface, relatively flush with superior disk 22. This smooth surface helps to minimize any irritation that may occur to the adjacent soft tissue. The fracturing of connecting rod 23 also serves to deform the threads of connecting rod 23, providing an additional anti-rotation feature.

Once fractured from the remainder of connecting rod 23, the excess portion of connecting rod 23 removed by installation tool 30 is retained within central cavity 34. This is due to the threaded coupling between connecting rod 23 and threaded region 36. This allows installation tool 30 and the excess portion of connecting rod 23 to be easily and conveniently discarded and helps to ensure that the excess portion of connecting rod 23 will not be misplaced or lost once removed from the rest of connecting rod 23.

Thus, once installed, cranial flap fixation device 20 provides a rigid fixation of a cranial flap to the adjacent cranial bone that offers greater variability in the amount of pressure to apply to the cranium, reduced irritation to soft tissues, and the ability to remove the fixation without undue effort. Furthermore, fixation device 20 may be configured to be installed using a disposable installation tool that significantly reduces surgical times by eliminating several time consuming steps required by previous clamp-type fixation devices.

Figure 4:
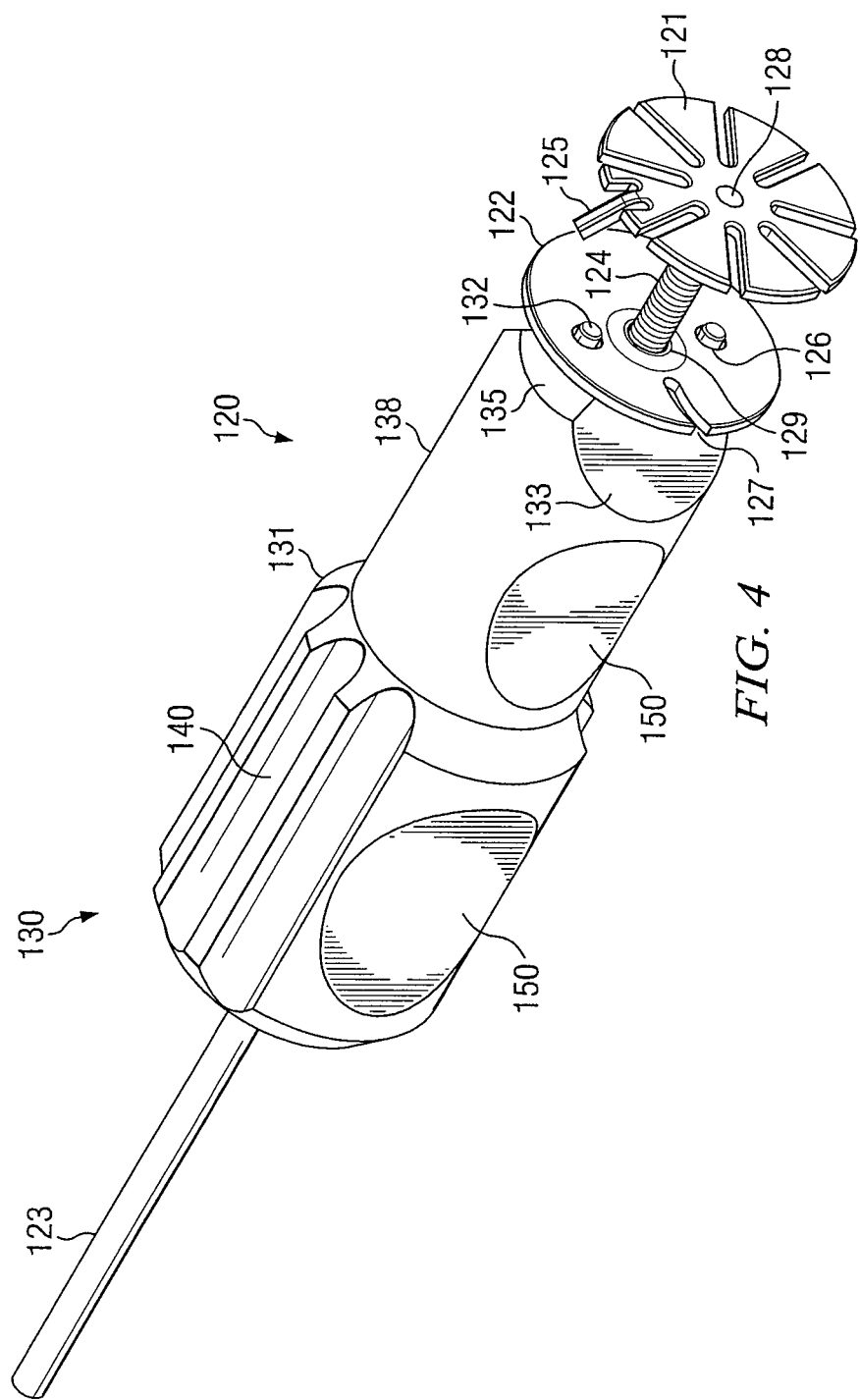
FIG. 4 illustrates an alternative embodiment of a cranial flap fixation device along with an installation tool in accordance with the present invention.

FIG. 4 illustrates an alternative embodiment of a cranial flap fixation device labeled fixation device 120. Like fixation device 20 discussed previously, fixation device 120 includes an elongate rod, labeled connecting rod 123. In the illustrated embodiment, connecting rod 123 includes a threaded region 124. In alternative embodiments, all of connecting rod 123 may by threaded.

One end of connecting rod 123 is coupled to an inferior disk 121 through a central orifice 128. Inferior disk 121 may be coupled to connecting rod 123 by being screwed onto threaded portion 124 of connecting rod 123. In alternative embodiments, inferior disk 121 may be coupled to connecting rod 123 by a separate screw into the end of connecting rod 123, inferior disk 121 could be welded to connecting rod 123, or the two pieces could be coupled in any other appropriate manner.

In the illustrated embodiment, inferior disk 121 includes an anti-rotation device in the form of an upward-facing tab 125, which is configured to be aligned with joint 13 between cranial flap 10 and surrounding cranial bone 11 (see FIG. 1). This provides the additional benefit of inhibiting the rotation of fixation device 20 after installation, which may loosen the connecting rod 123/superior disk 122 assembly. This allows for greater stability for the assembly once installed. In FIG. 4, tab 125 is shown as being formed by a cut-out in one flange of inferior disk 121. However, it should be recognized that tab 125 may be formed by other methods as well.

Also coupled to threaded region 124 are superior disk 122 and installation tool 130. Installation tool 130 and superior disk 122 interact in a similar manner as installation tool 30 and superior disk 22 discussed above. Installation tool 130 includes a plurality of pins 132 which engage the plurality of guide holes 126 located on superior disk 122. Because of this engagement, when installation tool 130 is rotated around the longitudinal axis of connecting rod 123, superior disk 122 is also rotated relative to connecting rod 123.

As shown in FIG. 4, installation tool 130 includes tool grip 131, which provides a handle for a surgeon to grip while tightening fixation device 120. As such, tool grip 131 may include a plurality of grooves 140 longitudinally disposed on the exterior of the grip 131, providing a surface for a surgeon to grip. In alternative embodiments, other gripping features may be used in lieu of or in addition to the longitudinal grooves 140. For example, knurled surfaces and/or other indentations may be provided.

Like installation tool 30, installation tool 130 may also be used to remove the excess portion of connecting rod 123 after fixation device 120 has been brought in intimate contact with the cranium. To help accomplish this, installation tool 130 includes two angled faces 133. In the illustrated embodiment, angled faces 133 form an approximately 90-degree angle with each other and contact superior disk 122. These angled faces 133 are used as a guide for installation tool 130 when installation tool 130 is used to remove the excess portion of connecting rod 123.

Once fixation device 120 is securely fastened to the cranium, installation tool 130 is tilted first in one direction and then in the opposite direction, using angled faces 133 as a guide. This back and forth bending is continued until it results in the intentional fracturing of connecting rod 123.

In the illustrated embodiment, installation tool 130 includes features to aid in the intentional fracturing of connecting rod 123. A first feature which facilitates fracturing of connecting rod 123 is the increased length of installation tool 130. The increased length of installation tool 130 provides greater leverage than would a shorter installation tool, and thereby decreases the force which must be imparted on installation tool 130 to fracture connecting rod 123. The length of installation tool 130 is not limited by any physical constraints inherent to the surgery. Therefore, installation tool 130 could be practically any length. In certain embodiments, connecting rod 123 may be used to prevent fixation device 120 from rotating as installation tool 130 is turned. In such an embodiment, installation tool 130 may be shorter than the portion of the connecting rod above the superior disk 122 to allow gripping of connecting rod 123. In certain alternative embodiments, installation tool 130 could be between one inch and six inches in length.

An additional feature of installation tool 130 which aids in the fracturing of connecting rod 123 is a reduced diameter portion 138. Reduced diameter portion 138 makes it easier for an installer to grip installation tool 130 as the contour of installation tool 130 more closely resembles the contours of a human thumb and forefinger, which may be used to grip installation tool 130. The diameter of reduced diameter portion 138 relative to the tool grip 131 could be practically any size to achieve a desired feel in an installers hand or to provide an adequate gripping surface. In one embodiment, the ratio of diameters between the reduced diameter portion 138 and the tool grip 131 could be between 0.95:1 and 0.5:1. Further, in the illustrated embodiment, the length of the reduced diameter portion 138 is approximately equal to the length of the tool grip 131. In alternative embodiments, the length of reduced diameter portion 138 and the length tool grip 131 could be practically any length and the length of one could be practically any ratio to the length of the other.

The diameter of installation tool 130 also aids in fracturing connecting rod 123. In the illustrated embodiment, installation tool 130 has a significantly larger diameter than connecting rod 123. In certain embodiments, the diameter of installation tool 130 could be between ten and twenty times greater than the diameter of the connecting rod. In alternative embodiments, the ratio of the diameters of connecting rod 123 and installation tool 130 could be practically any relation which allows the bending and fracturing of connecting rod 123 using installation tool 130.

Further grip enhancing features of installation tool 130 are finger divots 150 arranged on tool grip 131 and reduced diameter portion 138. Like reduced diameter portion 138, finger divots 150 more closely match the contours of human fingers and thereby increase the ability to tightly grip installation tool 130. These grip enhancing features of installation tool 130 reduce the chance of slippage and thereby ensure that the force used to fracture connection rod 123 is properly imparted through installation tool 130 into connection rod 123. In the illustrated embodiment, finger divots 150 are illustrated as shallow oblong depressions. In alternative embodiments, finger divots 150 may take practically any shape and be of practically any desired depth. The illustrated placement of finger divots 150 is not critical and finger divots 150 could be added, removed, or relocated without falling outside the scope of the present invention.

In practice, a surgeon may install fixation device 120 by placing inferior disk 121 under the surrounding cranial bone such that connecting rod 123 extends outward from the patient through a burr hole. The surgeon may then grip installation tool 130 or connecting rod 123 to slightly rotate the inferior disk such that tab 125 is properly positioned in the cut between the surrounding cranial bone and where the cranial flap will be replaced. The cranial flap may then be replaced. The surgeon may then firmly grip connecting rod 123 and installation tool 130 for the purpose of rotating installation tool 130 relative to connecting rod 123 such that the internal threads of installation tool 130 engage the external threads of threaded region 124 and thereby pull installation tool 130 toward inferior disk 121. The installation tool may be gripped on tool grip 131 and specifically at longitudinal grooves 140. Longitudinal grooves 130 will increase the surgeon's grip on tool grip 131 and reduce the chance of slipping.

The surgeon may then rotate installation tool 130 relative to connecting rod 123. As installation tool 130 is rotated, the threads of installation tool 130 engage the threads of threaded region 124 and move installation tool 130 toward the cranial flap and surrounding bone. As installation tool 131 moves, pins 132 engage the guide holes 126 on the superior disk 122 and force the superior disk 122 to rotate and move toward the cranial flap with the installation tool 130. The rotation of installation tool 130 and superior disk 122 will continue until superior disk 122 contacts the cranial flap and surrounding bone, and tab 127 is seated in the cut between the cranial flap and surrounding bone. In this position of fixation device 120, the cranial flap and surrounding bone are held on either side by inferior disk 121 and superior disk 122.

The surgeon may now remove installation tool 130 and the excess portion of connecting rod 123 by fracturing connecting rod 123 between installation tool 130 and superior disk 122. The surgeon may grip installation tool 130 by finger divots 150 and reduced diameter portion 138. Using these surfaces to insure an ample grip, the surgeon will then bend connecting rod 123, using installation tool 130, toward a first angled face 133. This first bend can continue until angled face 133 contacts superior disk 122. The surgeon may then bend connecting rod 123 in the opposite direction until a second angled face 133 contacts superior disk 122. Alternating between bending in these two directions can continue until connecting rod 123 fractures.

Although the illustrated embodiment and many embodiments disclosed within this specification focus primarily upon the use of cranial flap fixation device 20 for surgical procedures involving repair of the cranium, it will be recognized by those of ordinary skill in the art that cranial flap fixation device 20 has a substantial number of applications that are unrelated to the cranium. In practice, cranial flap fixation device 20 may be used to secure any two sections of bone, tendon, soft tissue and/or any combination thereof. Nothing within this specification should be interpreted to limit the teachings of the present invention to repair of the cranium.

Although a preferred embodiment of the method and apparatus of the present invention has been illustrated in the accompanying drawings and described in the foregoing detailed description, it will be understood that the invention is not limited to the embodiment disclosed, but is capable of numerous rearrangements, modifications, and substitutions without departing from the spirit of the invention as set forth and defined by the following claims.

What is claimed is:

1. A surgical fixation tool, comprising:
 a fixation device comprising:
  a connecting rod having a first end, second end, and an intermediate portion disposed between the first end and the second end;
  the connecting rod having a threaded portion disposed between the first end and the intermediate portion;
  an inferior disk coupled with the connecting rod proximate the first end of the connecting rod;
  a superior disk having an orifice through a central region of the superior disk;
  the orifice being sized to allow the superior disk to engage the threaded portion to movably couple the superior disk and the threaded portion;
 an installation tool having a central cavity extending through at least a portion of the installation tool;
 the central cavity being at least partially threaded;
 the installation tool being configured to install the fixation device by engaging the superior disk and the threaded portion, such that the superior disk becomes movably coupled to the threaded portion and rotation of the installation tool in a first direction directs the superior disk toward the inferior disk; and
 the installation tool being further configured to disengage from the superior disk and the threaded portion after installation of the fixation device, wherein the superior disk remains coupled to the threaded portion after the installation tool is disengaged from the superior disk and the threaded portion.

2. The surgical fixation tool of claim 1, wherein the orifice is sized to allow for installation of the superior disk over the second end of the connecting rod.

3. The surgical fixation tool of claim 1, further comprising a plurality of flange-forming slots radially disposed on the inferior disk, the flange-forming slots extending from an area adjacent a central portion of the inferior disk radially outward.

4. The surgical fixation tool of claim 1, further comprising an anti-rotation device disposed upon a face of the inferior disk, the anti-rotation device being configured to align with a joint between a cranial flap and adjacent bone to resist rotation of the inferior disk, with respect to the connecting rod, from an installed position.

5. The surgical fixation tool of claim 1, wherein a face of the superior disk opposite the inferior disk is concave with respect to the inferior disk.

6. The surgical fixation tool of claim 1, further comprising an anti-rotation device disposed upon a face of the superior disk, the anti-rotation device being configured to align with a joint between a cranial flap and adjacent bone to resist rotation of the superior disk, with respect to the connecting rod, from an installed position.

7. The surgical fixation tool of claim 1, wherein the installation tool is configured to allow for coupling of the installation tool over the second end of the connecting rod.

8. The surgical fixation tool of claim 1, wherein the installation tool is further configured to allow the installation tool to disengage from the superior disk when the superior disk is in contact with a cranial flap and adjacent bone after installation.

9. The surgical fixation tool of claim 1, wherein the connecting rod is formed of a material operable to fracture in response to bending forces.

10. The surgical fixation tool of claim 1, wherein the installation tool includes a first section and a second section and wherein a length to diameter ratio of the first section is larger than a length to diameter ratio of the second section.

11. The surgical fixation tool of claim 10, wherein the first section and the second section are approximately equal in length.

12. The surgical fixation tool of claim 1, wherein the installation tool includes a reduced diameter portion, and wherein a length of the reduced diameter portion is approximately one-half of a length of the installation tool.

13. The surgical fixation tool of claim 1, wherein the installation tool includes:
a plurality of oblong recesses disposed on a body of the installation tool;
the plurality of oblong recesses configured to provide gripping surfaces; and
the gripping surfaces being configured to accommodate tilting of the installation tool with respect to the superior disk for fracturing the connecting rod.

14. The surgical fixation tool of claim 1, wherein the installation tool includes:
a plurality of recessed channels longitudinally disposed on a body of the installation tool;
the recessed channels configured to provide gripping surfaces; and
the gripping surfaces being configured to accommodate turning the installation tool, and thereby change the orientation of the superior disk relative to the connecting rod.

15. The surgical fixation tool of claim 1, wherein a diameter of the installation tool is between ten and twenty times larger than a diameter of the connecting rod.

* * * * *

UNITED STATES PATENT AND TRADEMARK OFFICE
CERTIFICATE OF CORRECTION

| | | |
|---|---|---|
| PATENT NO. | : 8,771,322 B2 | Page 1 of 1 |
| APPLICATION NO. | : 12/334586 | |
| DATED | : July 8, 2014 | |
| INVENTOR(S) | : Ahmad et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1305 days.

Signed and Sealed this
First Day of September, 2015

Michelle K. Lee
*Director of the United States Patent and Trademark Office*